United States Patent
Blackledge et al.

(10) Patent No.: US 9,468,457 B2
(45) Date of Patent: Oct. 18, 2016

(54) ATHERECTOMY DEVICE WITH ECCENTRIC CROWN

(71) Applicant: Cardiovascular Systems, Inc., St. Paul, MN (US)

(72) Inventors: Victor Blackledge, Cologne, MN (US); Benjamin Haselman, St. Paul, MN (US); Joseph Higgins, Minnetonka, MN (US); Joseph Bahoora, Medina, MN (US); Nicholas Ellering, Crystal, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 165 days.

(21) Appl. No.: 14/071,111

(22) Filed: Nov. 4, 2013

(65) Prior Publication Data

US 2015/0094745 A1    Apr. 2, 2015

Related U.S. Application Data

(63) Continuation-in-part of application No. 14/041,559, filed on Sep. 30, 2013.

(51) Int. Cl.
| | |
|---|---|
| *A61B 17/22* | (2006.01) |
| *A61B 17/3207* | (2006.01) |
| *A61B 17/00* | (2006.01) |
| *A61B 17/32* | (2006.01) |

(52) U.S. Cl.
CPC .................. *A61B 17/320758* (2013.01); *A61B 2017/00526* (2013.01); *A61B 2017/320004* (2013.01); *A61B 2017/320766* (2013.01)

(58) Field of Classification Search
CPC .............. A61B 17/3207; A61B 2017/320741; A61B 17/32075; A61B 17/320758; A61B 2017/320766; A61B 2017/320056; A61B 17/32002; A61B 2017/320008; A61B 2017/320004
See application file for complete search history.

(56) References Cited

U.S. PATENT DOCUMENTS

| | | |
|---|---|---|
| 4,445,509 A | 5/1984 | Auth |
| 4,646,736 A | 3/1987 | Auth |
| 4,728,319 A | 3/1988 | Masch |
| 4,795,438 A | 1/1989 | Kensey et al. |
| 4,990,134 A | 2/1991 | Auth |
| 5,026,384 A | 6/1991 | Farr et al. |
| 5,030,201 A | 7/1991 | Palestrant |

(Continued)

OTHER PUBLICATIONS

Dictionary.com definition of swage as accessed Nov. 5, 2015; http://dictionary.reference.com/browse/swage.*

(Continued)

*Primary Examiner* — Jonathan Miles
(74) *Attorney, Agent, or Firm* — Barnes & Thornburg LLP; Jeffrey R. Stone (57) ABSTRACT

An atherectomy device may include an elongated, flexible drive shaft having a distal end for insertion into a vasculature of a patient and having a proximal end opposite the distal end remaining outside the vasculature of the patient, a handle coupled to the proximal end of the drive shaft for controlling the drive shaft, and a head arranged proximate the distal end of the drive shaft wherein the head may include a middle portion having a substantially uninterrupted outer surface and substantially conically-shaped first and second end portions, wherein the middle portion and substantially conically-shaped end portions all have a bore extending therethrough adapted to frictionally engage a drive shaft.

8 Claims, 10 Drawing Sheets

(56) References Cited

U.S. PATENT DOCUMENTS

| | | |
|---|---|---|
| 5,041,082 A | 8/1991 | Shiber |
| 5,078,723 A | 1/1992 | Dance et al. |
| 5,087,265 A | 2/1992 | Summers |
| 5,100,425 A | 3/1992 | Fischell et al. |
| 5,158,564 A | 10/1992 | Schnepp-Pesch et al. |
| 5,192,291 A | 3/1993 | Pannek, Jr. |
| 5,217,474 A | 6/1993 | Zacca et al. |
| 5,217,478 A | 6/1993 | Rexroth |
| 5,224,945 A | 7/1993 | Pannek, Jr. |
| 5,242,460 A | 9/1993 | Klein et al. |
| 5,242,461 A | 9/1993 | Kortenbach et al. |
| 5,261,877 A | 11/1993 | Fine et al. |
| 5,267,955 A | 12/1993 | Hanson |
| 5,308,354 A | 5/1994 | Zacca et al. |
| 5,312,427 A | 5/1994 | Shturman |
| 5,314,438 A | 5/1994 | Shturman |
| 5,358,485 A | 10/1994 | Vance et al. |
| 5,358,509 A | 10/1994 | Fine et al. |
| 5,360,432 A | 11/1994 | Shturman |
| 5,370,651 A | 12/1994 | Summers |
| 5,372,602 A | 12/1994 | Burke |
| 5,376,100 A | 12/1994 | Lefebvre |
| 5,395,311 A | 3/1995 | Andrews |
| 5,423,740 A | 6/1995 | Sullivan et al. |
| 5,423,846 A | 6/1995 | Fischell |
| 5,490,859 A | 2/1996 | Mische et al. |
| 5,501,694 A | 3/1996 | Ressemann et al. |
| 5,540,707 A | 7/1996 | Ressemann et al. |
| 5,584,843 A | 12/1996 | Wulfman et al. |
| 5,632,755 A | 5/1997 | Nordgren et al. |
| 5,792,157 A | 8/1998 | Mische et al. |
| 5,836,868 A | 11/1998 | Ressemann et al. |
| 5,888,200 A | 3/1999 | Walen |
| 5,916,227 A | 6/1999 | Keith et al. |
| 5,938,670 A | 8/1999 | Keith et al. |
| 5,968,064 A | 10/1999 | Selmon et al. |
| 6,015,420 A | 1/2000 | Wulfman et al. |
| 6,080,171 A | 6/2000 | Keith et al. |
| RE36,764 E | 7/2000 | Zacca et al. |
| 6,096,054 A | 8/2000 | Wyzgala et al. |
| 6,129,734 A | 10/2000 | Shturman et al. |
| 6,146,395 A | 11/2000 | Kanz et al. |
| 6,152,938 A | 11/2000 | Curry |
| 6,193,735 B1 | 2/2001 | Stevens |
| 6,217,595 B1 | 4/2001 | Shturman et al. |
| 6,270,509 B1 | 8/2001 | Barry et al. |
| 6,428,551 B1 | 8/2002 | Hall et al. |
| 6,436,111 B1 | 8/2002 | Kadavy et al. |
| 6,451,037 B1 | 9/2002 | Chandrasekaran et al. |
| 6,467,121 B1 | 10/2002 | Franzino et al. |
| 6,482,216 B1 | 11/2002 | Hiblar et al. |
| 6,494,890 B1 | 12/2002 | Shturman et al. |
| 6,503,261 B1 | 1/2003 | Bruneau et al. |
| 6,565,588 B1 | 5/2003 | Clement et al. |
| 6,579,299 B2 | 6/2003 | McGuckin, Jr. et al. |
| 6,596,005 B1 | 7/2003 | Kanz et al. |
| 6,616,676 B2 | 9/2003 | Bashiri et al. |
| 6,685,718 B1 | 2/2004 | Wyzgala et al. |
| 6,818,001 B2 | 11/2004 | Wulfman et al. |
| 6,818,005 B2 | 11/2004 | Kupferschmid et al. |
| 7,252,674 B2 | 8/2007 | Wyzgala et al. |
| 7,344,546 B2 | 3/2008 | Wulfman et al. |
| 7,507,245 B2 | 3/2009 | Shturman et al. |
| 7,584,022 B2 | 9/2009 | Shturman et al. |
| D607,102 S | 12/2009 | Robinson |
| D610,258 S | 2/2010 | Robinson |
| 7,674,272 B2 | 3/2010 | Torrance et al. |
| 7,713,231 B2 | 5/2010 | Wulfman et al. |
| 7,803,169 B2 | 9/2010 | Shamay |
| 8,177,801 B2 | 5/2012 | Kallok et al. |
| 8,337,516 B2 | 12/2012 | Escudero et al. |
| 8,348,965 B2 | 1/2013 | Prudnikov et al. |
| 8,353,923 B2 | 1/2013 | Shturman |
| 8,388,635 B2 | 3/2013 | Kumoyama et al. |
| 8,551,128 B2 | 10/2013 | Hanson et al. |
| 8,597,313 B2 | 12/2013 | Thatcher et al. |
| 8,628,550 B2 | 1/2014 | Narveson |
| 8,628,551 B2 | 1/2014 | Hanson et al. |
| 2001/0018596 A1 | 8/2001 | Selmon et al. |
| 2002/0077638 A1 | 6/2002 | Kadavy et al. |
| 2003/0125756 A1 | 7/2003 | Shturman et al. |
| 2003/0199889 A1 | 10/2003 | Kanz et al. |
| 2004/0006358 A1 | 1/2004 | Wulfman et al. |
| 2004/0097995 A1 | 5/2004 | Nash et al. |
| 2004/0220519 A1 | 11/2004 | Wulfman et al. |
| 2005/0149083 A1 | 7/2005 | Prudnikov et al. |
| 2005/0149084 A1 | 7/2005 | Kanz et al. |
| 2006/0142793 A9 | 6/2006 | Prudnikov et al. |
| 2007/0239140 A1 | 10/2007 | Chechelski et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0033423 A1 | 2/2008 | Peacock, III |
| 2008/0045986 A1 | 2/2008 | To et al. |
| 2008/0097500 A1 | 4/2008 | Nash et al. |
| 2008/0185419 A1 | 8/2008 | Smith et al. |
| 2008/0221601 A1 | 9/2008 | Huynh et al. |
| 2008/0228208 A1 | 9/2008 | Wulfman et al. |
| 2008/0306498 A1 | 12/2008 | Thatcher et al. |
| 2009/0069829 A1 | 3/2009 | Shturman |
| 2009/0099581 A1 | 4/2009 | Kim et al. |
| 2009/0105736 A1 | 4/2009 | Prudnikov et al. |
| 2009/0149877 A1 | 6/2009 | Hanson et al. |
| 2009/0306690 A1 | 12/2009 | Rivers et al. |
| 2010/0125276 A1 | 5/2010 | Palermo |
| 2010/0292720 A1 | 11/2010 | Thatcher et al. |
| 2011/0087254 A1 | 4/2011 | Welty |
| 2011/0112562 A1 | 5/2011 | Torrance |
| 2011/0202084 A1 | 8/2011 | Hoem et al. |
| 2011/0213391 A1 | 9/2011 | Rivers et al. |
| 2012/0197276 A1 | 8/2012 | Lupton et al. |
| 2013/0018398 A1 | 1/2013 | Rivers et al. |
| 2013/0018399 A1 | 1/2013 | Rivers et al. |
| 2013/0023913 A1 | 1/2013 | Rivers et al. |
| 2013/0090632 A1 | 4/2013 | Tahara et al. |

OTHER PUBLICATIONS

Merriam-Webster definition of monolithic as accessed Nov. 5, 2015; http://www.merriam-webster.com/dictionary/monolithic.*
International Preliminary Report on Patentability from related PCT application No. PCT/US2014/050741; mailed Apr. 14, 2016.
International Preliminary Report on Patentability from related PCT application No. PCT/US2014/050723; mailed Apr. 14, 2016.

* cited by examiner

Fig. 14

ATHERECTOMY DEVICE WITH ECCENTRIC CROWN

CROSS-REFERENCE TO RELATED APPLICATIONS

This is a continuation-in-part application of patent application Ser. No. 14/041,559 filed Sep. 30, 2013, which is incorporated by reference.

BACKGROUND OF THE INVENTION

1. Field of the Invention

The invention relates to devices and methods for removing tissue from body passageways, such as removal of atherosclerotic plaque from arteries, utilizing a high-speed rotational atherectomy device. More particularly, the present invention relates to attachment of heads that may be used with an atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. The disclosure of U.S. Pat. No. 5,314,438 is hereby incorporated by reference in its entirety.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, in this prior art device, the center of mass offset from the rotational axis of the drive shaft would result in development of significant centrifugal force, exerting too much pressure on the wall of the artery and creating too much heat and excessively large particles.

U.S. Pat. No. 5,584,843 (Wulfman) discloses one or more ellipsoidal burrs or cuffs attached to a flexible drive shaft. The drive shaft is placed over a preformed shaped guidewire so that the drive shaft and burrs conform to the shape and profile of the guide wire, i.e., a gentle "S" or "cork-screw" shape. Wulfman, however, requires the preformed guidewire to achieve the non-linear shaping of the drive shaft, a deformed shaping state that is, therefore, present when the device is not rotated. Thus, Wulfman's burrs comprise a sweeping diameter that is limited to, and by, the guidewire shaping. In addition, each of Wulfman's burrs are elliptical and symmetric about the rotational axis of the drive shaft with each center of mass for the burrs being on the drive shaft's rotational axis. Thus, the sweeping diameter of Wulfman is not induced by rotational speed and, therefore, cannot be controlled other than by the guidewire's shaping. Difficulties in positioning the shaped, undeformed, guidewire without damaging the patient's vasculature are also present.

In many of the above-described devices, the mentioned burrs may be secured to the drive shaft with a slip fit that engages the drive shaft relatively loosely if at all. The burrs may then be otherwise secured to the drive shaft with brazing or soldering, for example, which can be inconsistent. The present invention helps to overcome these inconsistencies.

BRIEF SUMMARY OF THE INVENTION

In some embodiments, an atherectomy device may include an elongated, flexible drive shaft having a distal end for insertion into a vasculature of a patient and having a proximal end opposite the distal end remaining outside the vasculature of the patient. The device may also include a handle coupled to the proximal end of the drive shaft for controlling the drive shaft. The device may also include a head arranged proximate the distal end of the drive shaft. The head may include a middle portion having a substantially uninterrupted outer surface and substantially conically-shaped first and second end portions. The middle portion and substantially conically-shaped end portions may all include a bore extending therethrough that is adapted to frictionally engage a drive shaft.

In other embodiments, a head for an atherectomy device may include a middle portion having a substantially uninterrupted outer surface. The head may also include substantially conically-shaped first and second end portions. The middle portion and substantially conically-shaped end portions may all include a bore extending therethrough adapted to frictionally engage a drive shaft.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
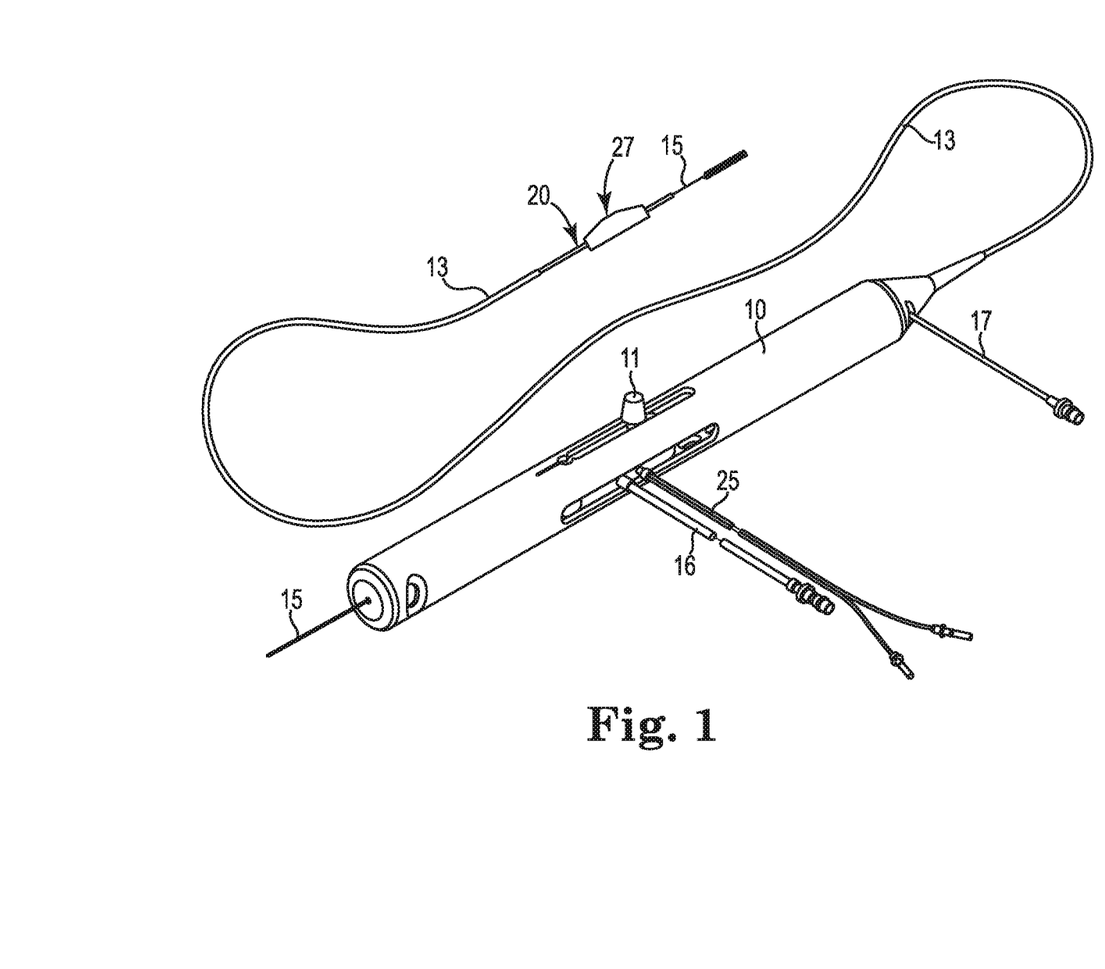
FIG. 1 is a perspective view of an atherectomy device, according to some embodiments.
Figure 2:
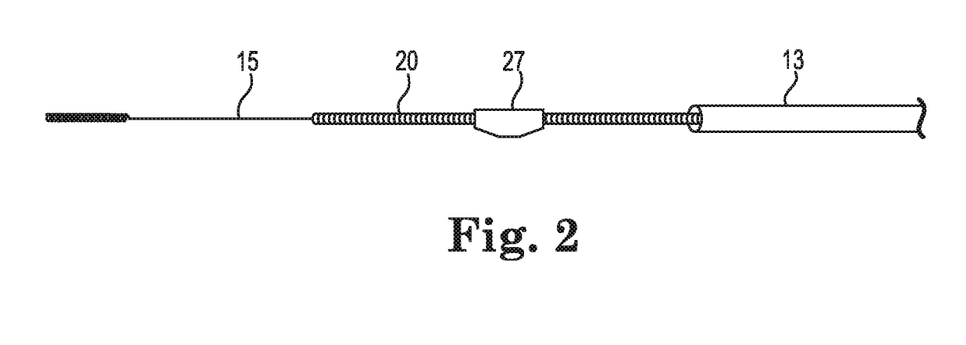
FIG. 2 is a side and partial cutaway view of the atherectomy device of FIG. 1.

FIG. 1 illustrates one embodiment of a rotational atherectomy device. As shown, the device may include a handle portion 10, an elongated, flexible drive shaft 20 having a head 27 in the form of a burr, crown, or bit, and an elongated catheter 13 extending distally from the handle portion 10. The drive shaft 20 may be constructed from helically coiled wire as is known in the art and the head 27 may be attached thereto. The catheter 13 may include a lumen in which most of the length of the drive shaft 20 is disposed, except for the head 27 and, in some cases, a short section distal to the head 27. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 may include a turbine (or similar rotational drive mechanism) for rotating the drive shaft 20 at high speeds. The handle 10 typically may be connected to a power source, such as compressed air delivered through a tube 16 or electrical power delivered with an electrical connection. A pair of fiber optic cables 25, or a single fiber optic cable, for example, may also be provided for monitoring the speed of rotation of the turbine and drive shaft 20. Details regarding such handles and associated instrumentation are well known in the industry. The handle 10 also may include a control knob 11 for advancing and retracting the turbine and drive shaft 20 with respect to the catheter 13 and the body of the handle.

As will be appreciated, there are several different types of heads 27 that may be provided for use in an atherectomy process. In some embodiments, a relatively symmetrical head may be used and in other embodiments an asymmetric head 27 may be provided such that a rotational eccentricity may be provided to increase the diameter of the path that the head 27 travels when rotated. In some embodiments, the head 27 may include a peripheral abrading surface for purposes of increasing the head's ability to clear away stenotic material. In any case, the head 27 may include a drive shaft 20 engagement feature such as a longitudinal bore or other receiving area for attaching the head 27 to the drive shaft 20.

Figure 3:
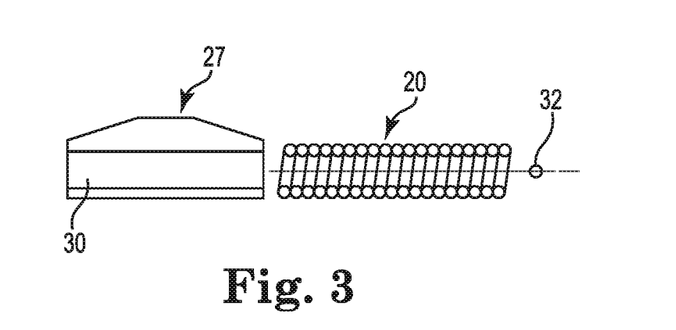
FIG. 3 is a close-up view of a head adjacent a distal end of a drive shaft, according to some embodiments.
Figure 4:
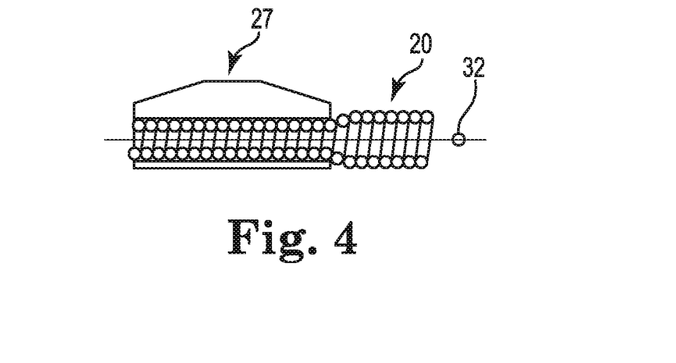
FIG. 4 is a close-up view of the head and distal end of the drive shaft of FIG. 3, with the head installed on the drive shaft.

In some cases, the head 27 may include a bore 30 having a diameter that is the same as or just slightly smaller than the outer diameter of the drive shaft 20 and the head 27 may be slip-fit onto the drive shaft. However, it is advantageous to have a fit that is more snug than the slip fit described. A more snug fit, or friction fit, may be provided by providing a head 27 with a bore diameter smaller than the outer diameter of the drive shaft 20. As shown by comparing FIG. 3 to FIG. 4, a friction fit may be provided by elastically reducing the diameter of the drive shaft 20 at a location where the head 27 is to be placed, placing the head 27, and releasing the drive shaft 20 so as to allow it to tend back toward its non-deformed shape. The confining geometry of the head 27 may create a friction fit between the portion of the drive shaft 20 within the head 27 because the drive shaft 20 may be tending toward or biased toward the larger diameter causing the portion of the drive shaft 20 within the head 27 to press radially outwardly against the internal wall of the bore 30, for example. Depending on the type of head 27 that is provided and the details of the drive shaft 20, several techniques may be used to secure the head 27 to the drive shaft 20. In some embodiments, the drive shaft 20 may be turned down, which is to say that the drive shaft 20 may be twisted about its longitudinal axis 32 in a direction causing the coil to tighten, thereby reducing the diameter. That is, for example, in FIG. 3, if the right portion of the drive shaft 20 is held stationary, while the left portion of the drive shaft 20 is twisted clockwise when viewed from the left, the coil may tighten and the diameter may be reduced. As can be appreciated from a review of FIGS. 3 and 4, it can be difficult to engage the distal end of the drive shaft 20 so as to perform the turning down process, while also placing the head 27. That is, if the distal end of the drive shaft 20 is engaged with a tool, for example, the tool may be in the way of placing the head 27. Accordingly, several approaches to solving this problem are provided herein.

Figure 5A:
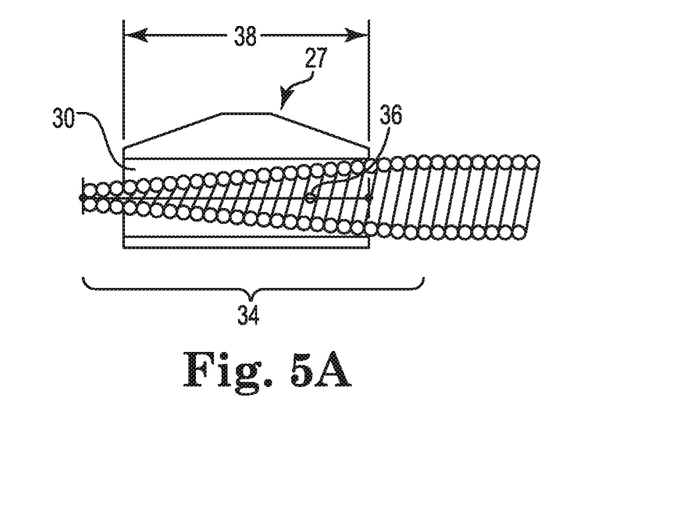
FIG. 5A is a close-up view of a head arranged on a tapered tip of a drive shaft, according to some embodiments.
Figure 5B:
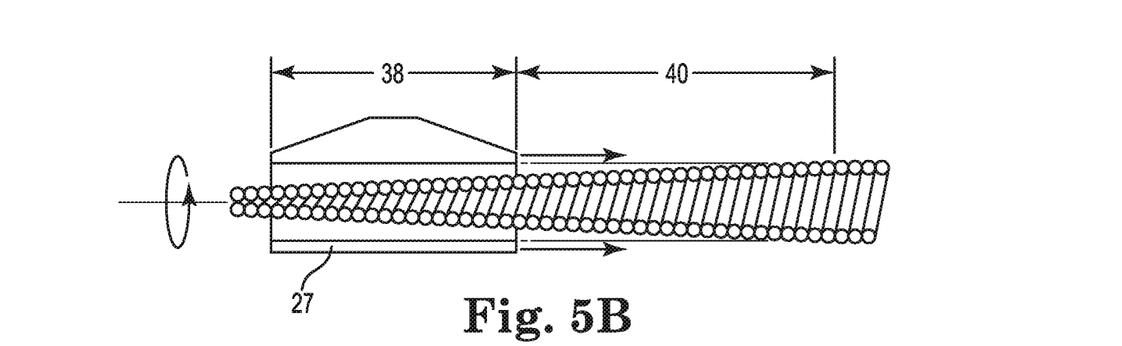
FIG. 5B is a close-up view of a head and tapered tip of FIG. 5A with a portion of the drive shaft having been turned down.
Figure 5C:
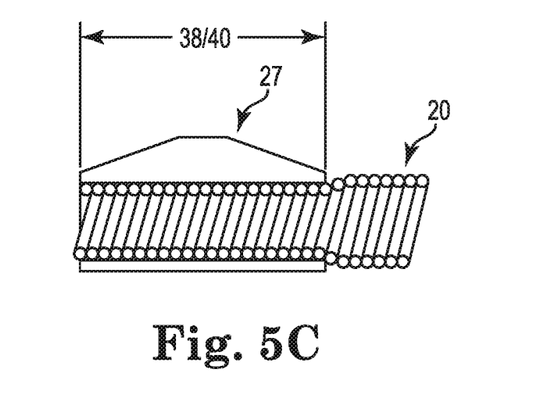
FIG. 5C is a close-up view of the head and drive shaft of FIG. 5A with the head in place on the drive shaft and the tapered tip having been trimmed off.

Referring to FIGS. 5A-5C, one embodiment of installing the head 27 is shown. In this embodiment, the drive shaft 20 may be provided with a tapered distal tip 34. The tapered distal tip 34 may have a gradually decreasing diameter as the tip extends distally. At a point along the tapered distal tip 34, the diameter of the tapered tip 34 may be approximately equal to the inner diameter or other cross-sectional dimension of the receiving feature 30, or bore, of the head 27. As the tapered tip 34 extends further distal, the diameter of the tip 34 may continue to decrease at a selected rate. The rate of taper may be selected such that the length 36 of the tapered tip 34, from the point where the diameter of the tip 34 is equal to the inner diameter of the bore 30, is at least slightly longer than the length 38 of the head 27. As such, and as shown in FIG. 5A, the head 27 may be placed on the tapered tip 34 and a portion of the tapered tip 34 may extend out the distal end of the head 27 when the head 27 encounters the tapered tip 34 diameter stopping it from moving further proximally.

The geometry of the tapered tip 34 may therefore be selected to allow the distal tip to project from the distal end of the head 27 when the head 27 is placed on the tapered tip 34. This geometry may allow the distal tip of the taper 34 to be engaged by a turning tool, such that the drive shaft 20 may be turned down and the head 27 may be moved proximally as shown in FIG. 5B without interfering with the turning tool. That is, as shown in FIG. 5B, the turning tool may engage the distal tip of the taper 34 and may turn the tip clockwise when viewed from the left and, assuming that a proximal portion of the drive shaft 20 is held stationary, the turning of the distal tip may cause a length of the drive shaft to be turned down as shown in FIG. 5B. The drive shaft 20 may be turned down by continuing to rotate the distal tip until a length of the drive shaft sufficient to secure the head 27 has a reduced diameter. For example, in one embodiment, a length 40 of the drive shaft proximal to the tapered tip 34 may be turned down and the length 40 of that portion may be approximately equal to the length 38 of the head 27.

Once a sufficient length of the drive shaft 20 has had its diameter reduced, the head 27 may be moved proximally over the turned down portion. Once the head 27 has been placed as desired, the distal tip of the drive shaft 20 may be released, or alternatively unwound, thereby causing the portion of the drive shaft within the head 27 to attempt to return to its original size. As will be appreciated, the inner diameter, or other internal cross-sectional dimension, of the head 27 will confine the drive shaft 20 to a smaller diameter than its at rest diameter causing the drive shaft 20 to press outwardly on the inner surface of the head 27 creating a friction fit. Once the head 27 is in place, the tapered tip 34 may be clipped off, or otherwise removed allowing the inner lumen of the drive shaft 20 to be available for passing through of a guidewire, for example.

In addition to the friction fit provided, the head 27 may also be secured to the drive shaft 20 with a secondary treatment. For example, in some embodiments, the head 27 may also be brazed to the drive shaft. In other embodiments, the head 27 may be welded, soldered, adhered, or otherwise affixed to the drive shaft 20. Still other secondary treatments may be provided for securing the head 27 to the drive shaft 20.

The tapered tip 34 may be pre-treated to allow the handling of the tip as described. That is, in some embodiments the tapered tip 34 may be heat-treated to harden the tip 34 and resist deformations when the tip 34 is gripped or otherwise engaged for the turning down process. In other embodiments, the tapered tip 34 may be brazed, welded, filled, or otherwise treated to resist collapse or deformation under the gripping or other engaging forces used during the turning down process. However, it is to be appreciated that where brazing, welding, filling, or other techniques are used, such techniques may be limited to portions of the tapered tip 34 that have diameters less than the inner diameter of the head 27 so as to avoid a situation where a portion of the tapered tip 34 is both larger than the inner diameter of the head 27 and also resists reduction in size wherein the head 27 may be more difficult or even prevented from being properly positioned.

It is to be appreciated that the turning down of the drive shaft 20 may be performed elastically. That is, the amount of reduction in the diameter may be such that the bending caused in the windings of the drive shaft 20 are limited to elastic bending forces such that, when released, the drive shaft 20 will tend toward returning to its previous size and shape. It is also to be appreciated that, due to the friction between the windings of the drive shaft 20, the effect of the turning down of the distal tip on the diameter of the drive shaft 20 may be reduced as you move proximally along the drive shaft 20. (i.e., away from point where the turning is imparted) This effect may be adjusted or modified depending on how much of, and at what location, the proximal portion of the drive shaft 20 is held stationary.

It is also to be appreciated that while the head 27 is shown to be positioned immediately proximal to the distal end of the drive shaft 20, the drive shaft 20 may be turned down for a longer length in FIG. 5B, allowing the head 27 to be slid further proximally along the drive shaft 20 leaving a longer length of the drive shaft 20 distal to the head 27. Still further, in some embodiments, additional heads 27 may also be installed. In some embodiments a first head 27A may be installed and brazed, soldered, welded, or otherwise secured in place. After installation of the first head 27A, a second head 27B may be installed by turning down the portion of the shaft 20 that is distal to the first head 27A. The second head 27B may then also be brazed soldered, welded, or otherwise secured. In other embodiments, the drive shaft 20 may be turned down and each head 27A, 27B may be properly positioned before any brazing, soldering, welding, or other securing process is performed. In some embodiments, the length of the tapered tip 34 on the drive shaft 20 may be sufficient to allow multiple heads 27 to be placed on the tapered tip 34 such that once the drive shaft 20 is turned down, each of the multiple heads 27A, 27B may be positioned as desired without having to disengage the turning tool to insert an additional head 27.

Figure 6A:
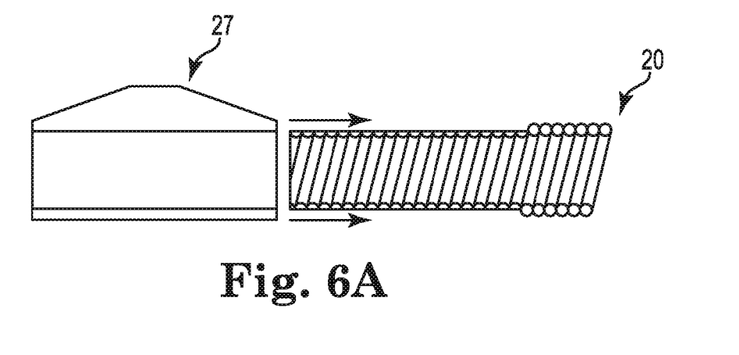
FIG. 6A is a close-up view of a head adjacent a ground down distal end of a drive shaft.
Figure 6B:
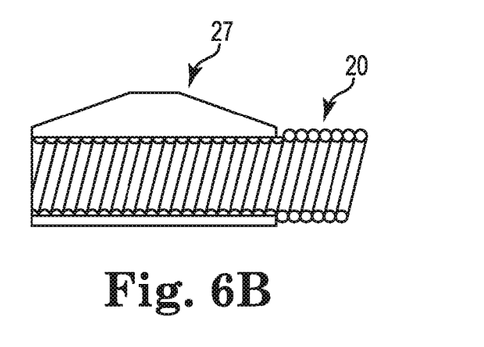
FIG. 6B is a close-up view of the head and distal end of FIG. 6A with the head in place on the distal end of the drive shaft.

Turning now to FIGS. 6A-6B, a different process for seating a head 27 on a drive shaft 20 is shown. In this embodiment, the diameter of the drive shaft 20 is such that the outer diameter of the drive shaft 20 is larger than the inner diameter of the head 27, but the inner diameter of the drive shaft 20 is smaller than the inner diameter of the head 27. As such, when a portion of the drive shaft 20 is ground away, the drive shaft 20 may be provided with an outer diameter that is the same or similar to the inner diameter of the head 27 allowing the head 27 to be slipped onto the drive shaft 20 and secured.

As with the embodiment of FIGS. 5A-5B, it is to be appreciated that while the head 27 is shown to be positioned immediately proximal to the distal end of the drive shaft 20, the head 27 may be positioned further proximally along the drive shaft 20 leaving a longer length of the drive shaft 20 distal to the head 27. In this embodiment, a longer length of the drive shaft 20 may be ground down. However, in other embodiments, only the portion of the drive shaft 20 where the head is to be seated may be ground down and the portion of the drive shaft distal to the head location may be turned down to allow the head 27 to be slid along the drive shaft 20 to the ground down location. As such, a combination of the turning down approaches as well as the grinding approach may be employed. Still further, in some embodiments, additional heads 27 may also be installed.

Figure 7A:
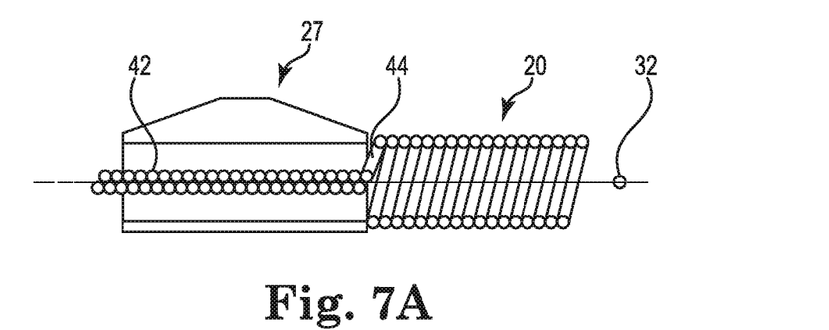
FIG. 7A is a close-up view of a head arranged on a tightly wound extension of a drive shaft, according to some embodiments.
Figure 7B:
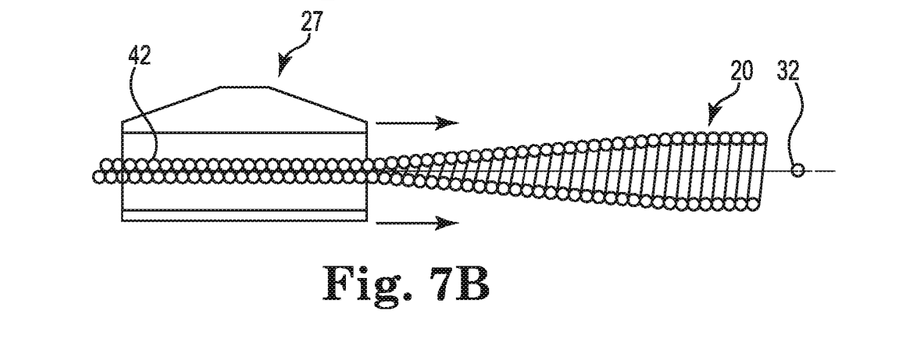
FIG. 7B is a close-up view of the head and drive shaft of 7A with a portion of the drive shaft having been turned down.

Turning now to FIGS. 7A-7B, an additional embodiment is shown for turning down the drive shaft 20 to allow placement of the head 27. In this embodiment, the distal tip of the drive shaft 20 includes a tightly wound extension 42 extending from its distal end. The tightly wound extension 42 may provide a rotational resistance higher than that of the drive shaft 20 because of its tightly wound geometry. Accordingly, as shown in FIG. 7B, the tightly wound extension 42 may be used by gripping the extension 42 distal to the head 27, turning down a length of the drive shaft 20, and allowing the head 27 to be slipped proximally to a selected location. Upon release or unwinding of the extension 42, the drive shaft 20 may engage the inner bore 30 of the head 27 with a friction fit. The head 27 may then be secured with brazing, welding, soldering, or other securing means.

It is to be appreciated that while the tightly wound extension 42 is shown to be arranged along the longitudinal axis 32 of the drive shaft 20, the extension 42 may also extend parallel to the longitudinal axis 32, but in line with an outer periphery of the drive shaft 20. This may avoid encountering bending forces that may be too high for the arm 44 shown in FIG. 7A that extends from the periphery inwardly to the longitudinal axis. Where the extension 42 is provided in line with the outer periphery of the shaft 20, as the turning down process is performed, the extension may be forced into closer alignment with the longitudinal as shown in FIG. 7B.

Like the tapered tip 34, the tightly wound extension 42 may have a length at least slightly longer than the head 27 such that the distal end of the tightly wound extension 42 may be engaged by a gripping tool or other engaging too while the head 27 is in place thereon. In other embodiments, as also mentioned with respect to the tapered tip 34, the length of the tightly wound extension 42 may be selected to allow one or more heads 27 to be placed thereon such that one step of turning down the drive shaft 20 may allow placement of the one or more heads 27. In addition, and again like the tapered tip 34, all or a portion of the tightly wound extension 42 may be heat treated, brazed, soldered, or welded to provide a stronger member capable of withstanding the gripping or other engaging pressures encountered from the gripping or engaging tool.

It is to be appreciated that the methods shown in FIGS. 5A-5C and 7A-7B involve drive shaft geometries that extend through the head 27 allowing the distal tip of the drive shaft 20 to be gripped or engaged such that the turning down method may be performed. However, an alternative approach may include providing a drive shaft 20 without particularly adapted features and, instead, providing a tool or tools that may be inserted through the head 27 and may be adapted to grip or otherwise engage the distal end of the drive shaft 20, turn it down, and allow the head 27 to be positioned thereon.

Figure 8:
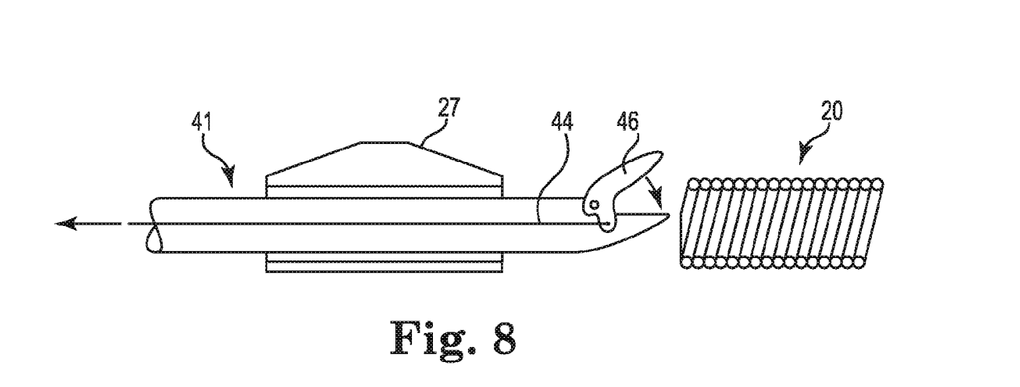
FIG. 8 is a side view of a tool for use in turning down a distal end of a drive shaft, according to some embodiments.

FIG. 8 shows a gripping tool 41 that may be used to extend through the head 27, grip the distal tip of the drive shaft 20 (e.g., the distal winding) and turn down the drive shaft 20. The tool 41 may be relatively long and slender and may have an actuation element 44 extending along its length for actuating a jaw or jaws 46 that may be used to grip the drive shaft 20. The tool 41 may include an actuation handle for pulling on the actuation element 44 and the handle may include a pistol type grip, a pliers type grip, or a rotational actuation may be used such that the initial rotation may cause the jaws 46 to engage the drive shaft 20 and further rotation may cause the drive shaft 20 to be turned down.

Figure 9:
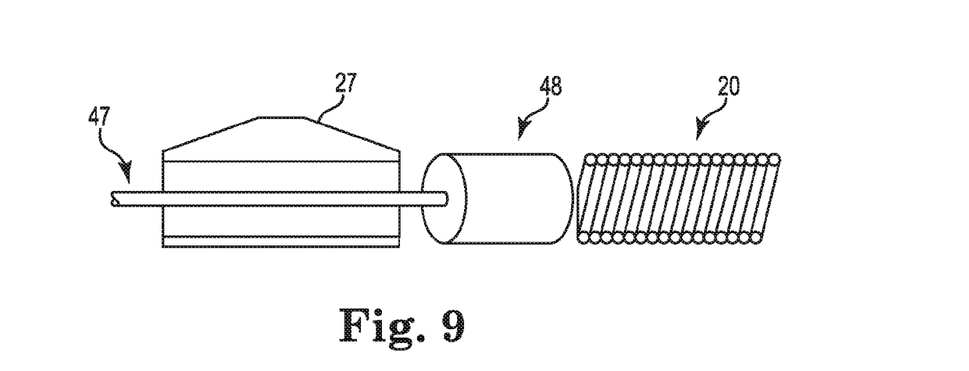
FIG. 9 is a side view of another tool for use in turning down a distal end of a drive shaft, according to some embodiments.

FIG. 9 shows still another tool 47 that may be used to turn down the drive shaft 20. In this embodiment, the tool 47 may include a resilient plug 48 that is slightly larger than the internal diameter of the drive shaft 20 in its uncompressed condition. As such, the plug 48 may be forced into the distal end of the drive shaft 20 thereby frictionally engaging the inner surface of the drive shaft 20. The tool 47 may then be rotated causing the drive shaft 20 to rotate and turn down thereby increasing the frictional engagement of the plug 48 with the drive shaft 20 and also compressing the plug 48 of the tool 47. A head 27 may be positioned on the shaft 20 of the tool 47 by either having forced the plug 48 of the tool 47 through the head 27 or by backing the shaft of the tool 47 through the head 27 and engaging the shaft with a handle or turning tool, for example. Once the drive shaft 20 is turned down sufficiently, the head 27 may be moved proximally onto the drive shaft 20. The positioned of the head 27 may be proximal to the resilient plug 48 such that once the head 27 is placed, the tool 47 may be released or unwound thereby releasing the engagement of the drive shaft 20 with the resilient plug 48. If the excess portion of the drive shaft 20 distal to the head 27 is not desired, the excess portion may be trimmed off.

Figure 10:
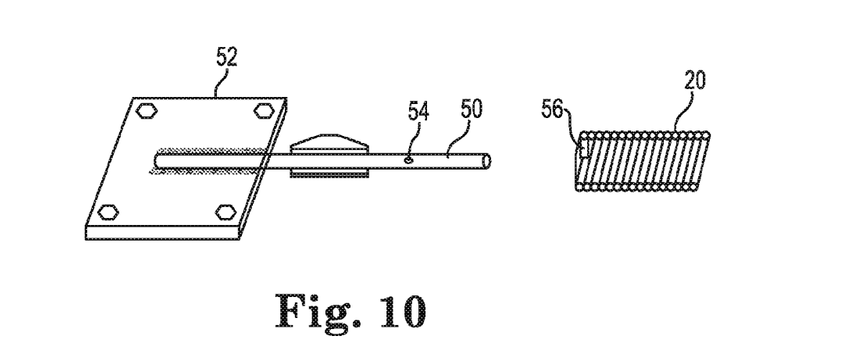
FIG. 10 is a perspective view of a mandrel for use in turning down a distal end of a drive shaft, according to some embodiments.

In addition to particular drive shaft adaptations and particular tools that may be used to "reach" through the head 27, another approach shown in FIG. 10 may be to use a mandrel 50 with a diameter adapted for installing the heads 27. As shown, the mandrel 50 may be supported off of a stationary base 52. Alternatively, the mandrel 50 may be held in a user's hand. The mandrel 50 may have a length suitable for placement of one or more heads 27 poised for installation on a drive shaft 20. The mandrel 50 may have an outside diameter less than the inner diameter of the heads 27 and allowing for the thickness of the windings of the drive shaft 20. In addition, adjacent the area for storing heads 27, the mandrel 50 may include an engagement feature 54 for engaging the distal end of the drive shaft 20. In some embodiments, for example, the mandrel 50 may include a hole with a diameter slightly larger than the thickness/diameter of the windings of the drive shaft 20. Other engagement features 54 for engaging the end winding of the drive shaft 20 may also be provided. The distal tip of the drive shaft 20 may have a length 56 of the final winding bent radially inward toward the longitudinal axis of the drive shaft 20. The drive shaft 20 may, thus, be placed onto the mandrel 50 and the bent portion 56 of the final winding may be placed in the hole in the mandrel 50 thereby securing the distal end of the drive shaft 20 against rotation. The remaining portion of the drive shaft 20 may thus be rotated to turn down the drive shaft 20 allowing the heads 27 in the storage area of the mandrel 50 to be moved into place on the drive shaft 20. As with the other embodiments, multiple heads 27 may be placed and each may be secured with brazing, welding, soldering, adhering, or other securing means.

Figure 11:
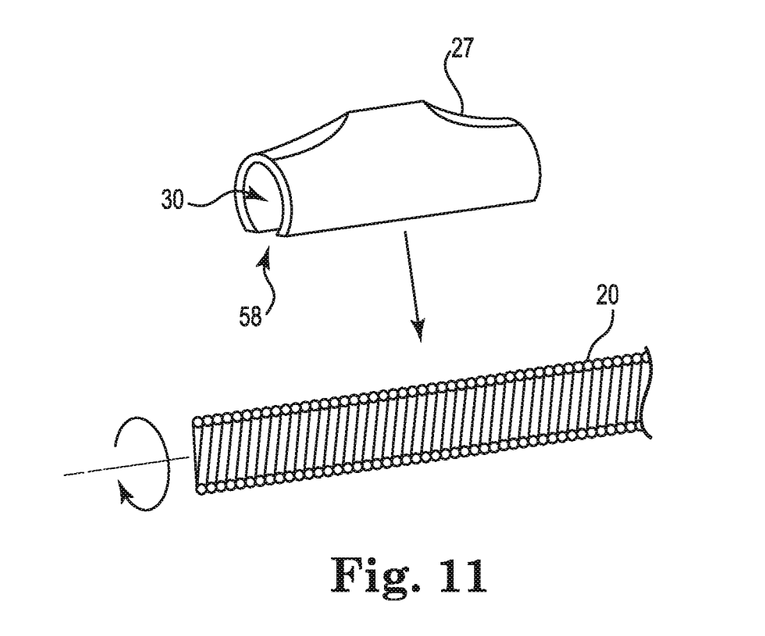
FIG. 11 is a perspective view of a drive shaft and a head adapted for engaging the drive shaft from the side, according to some embodiments.

In still other embodiments, a more conventional drive shaft 20 may be provided and more conventional tools may be used to grip and/or engage the drive shaft 20 such that it may be turned down. In this embodiment, as shown in FIG. 11, the head 27 may be provided with a longitudinally extending slot 58 having a width approximately as wide as the bore 30 diameter. In this embodiment, the drive shaft 20 may be turned down to reduce its diameter and the head 27 may be installed from the side, as shown. Like the other embodiments, the head 27 may be brazed, soldered, welded, or otherwise secured to the drive shaft 20 one it is in place and frictionally engaged.

It is to be appreciated, however, that the nature of the turning down methods described herein together with the higher frictional engagement of the head 27 with the shaft may allow for a head having a geometry not previously known. That is, the heads 27 shown in FIGS. 1-10 have previously been provided with a slot as shown and described in FIG. 11. This slot allowed for the head to be positioned on the drive shaft and allowed for an edge length to be available for soldering, brazing, welding, or otherwise securing the head to the drive shaft. With the method described herein, a head akin to those shown in FIGS. 1-10 and show in more detail in FIGS. 12-14 may be provided.

Figure 12:
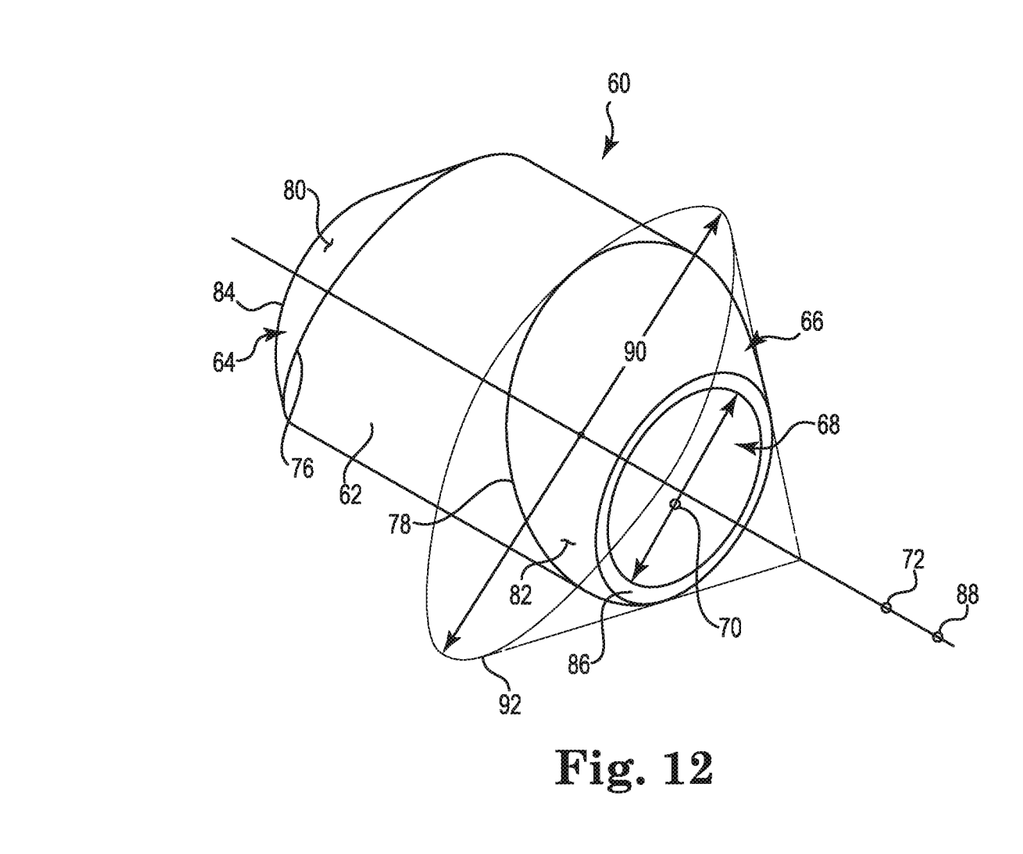
FIG. 12 is a perspective view of a head for an atherectomy device, according to some embodiments.

FIG. 12 shows a perspective view of a head 60 for arrangement on the distal end of a drive shaft 20 of an atherectomy device such as the device shown in FIG. 1. The head 60 may have an eccentric shape, as shown, or the head 60 may be symmetrical about a longitudinal axis, for example. The head 60 may include a middle portion 62 and two end portions 64, 66. Each of the middle portion 62 and end portions 64,66 may include a bore 68 extending therethrough and the bore 68 may be adapted for engaging a drive shaft 20. That is, the diameter 70 of the bore 68 may be slightly smaller than the outside diameter of the drive shaft 20 to allow for a friction fit. The head 60 may be installed on a drive shaft 20 according to one or more of the methods described above with respect to FIGS. 1-10.

The middle portion 62 of the head may include an outer surface that is substantially cylindrical and uninterrupted. That is, when viewed from the end as in FIG. 14, for example, the outer surface may be substantially circular and may be substantially uninterrupted (i.e., without a slot formed therein, for example). While a substantially cylindrical shape with a circular cross-section has been shown for the middle portion 62, it is to be appreciated that the cross-sectional shape may be elliptical, oval, oblong, or otherwise shaped to increase and/or control the level of eccentricity provided by the head 60. In some embodiments, an abrasive texture may be provided on the outer surface of the middle portion 62 of the head 60.

Figure 14:
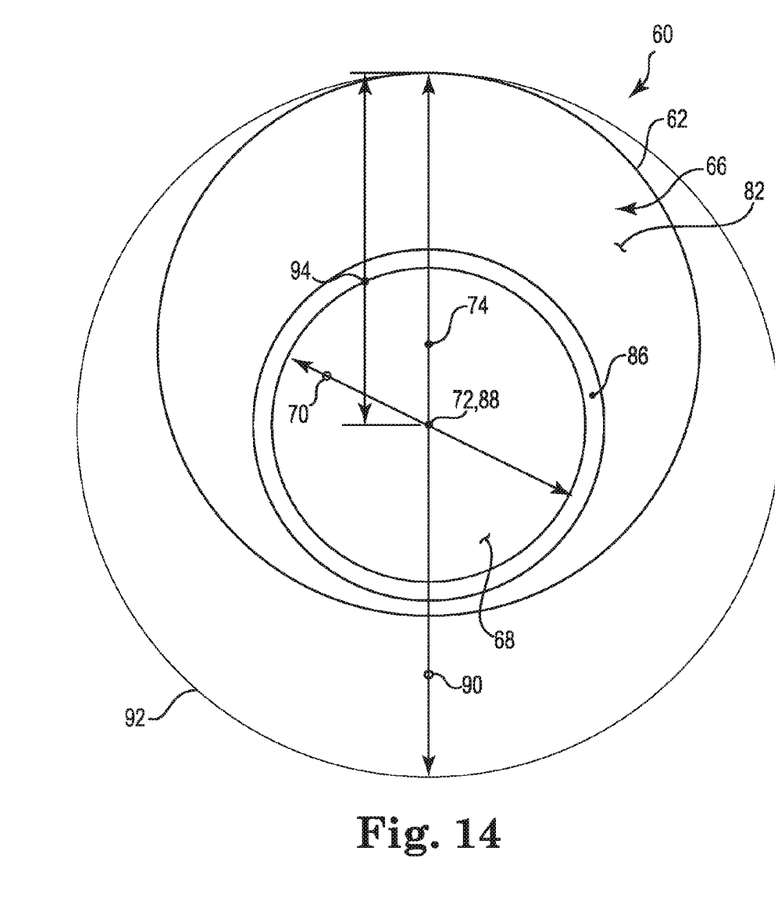
FIG. 14 is an end view thereof.

The bore 68 may be arranged to extend through the middle portion and may include a longitudinal axis 72 that is offset from the longitudinal axis 74 of the middle portion 62 as shown in FIG. 14. As such, the center of gravity of the middle portion 62 may be offset from the axis 72 of the bore 68 and, thus, when the drive shaft 20 rotates, the head 60 may be caused to follow a rotational path having a diameter and allowing the head 60 to effectively clear a vessel with a diameter larger than the outside diameter or dimension of the head. In other embodiments, the axis 72 of the bore 68 may be aligned with the axis 74 of the middle portion 62 such that the bore 68 is concentric with the outside surface of the middle portion 62. In these embodiments, a geometrically symmetric head may be provided and the material that the head 60 is constructed from may vary from one portion to another. As such, while the geometry of the head 60 may be symmetrical about a longitudinal axis 74, the center of gravity may still fall at a location in the cross-section that is offset from the geometrical longitudinal axis 74 allowing for an increase in the path of travel during rotation and allowing for an area larger than the diameter of the head 60 to be cleared.

The middle portion 62 may be substantially monolithic and/or solid, except for the bore 68 passing through the middle portion 62. In other embodiments, the middle portion 62 may be substantially shell like and may include ribs or braces extending inwardly from an outer shell portion to a wall of the bore 68 for maintaining the relative position of the outer shell relative to the bore 68. In still other embodiments, the middle portion 62 may be partially solid and shell-like in other areas.

Figure 13:
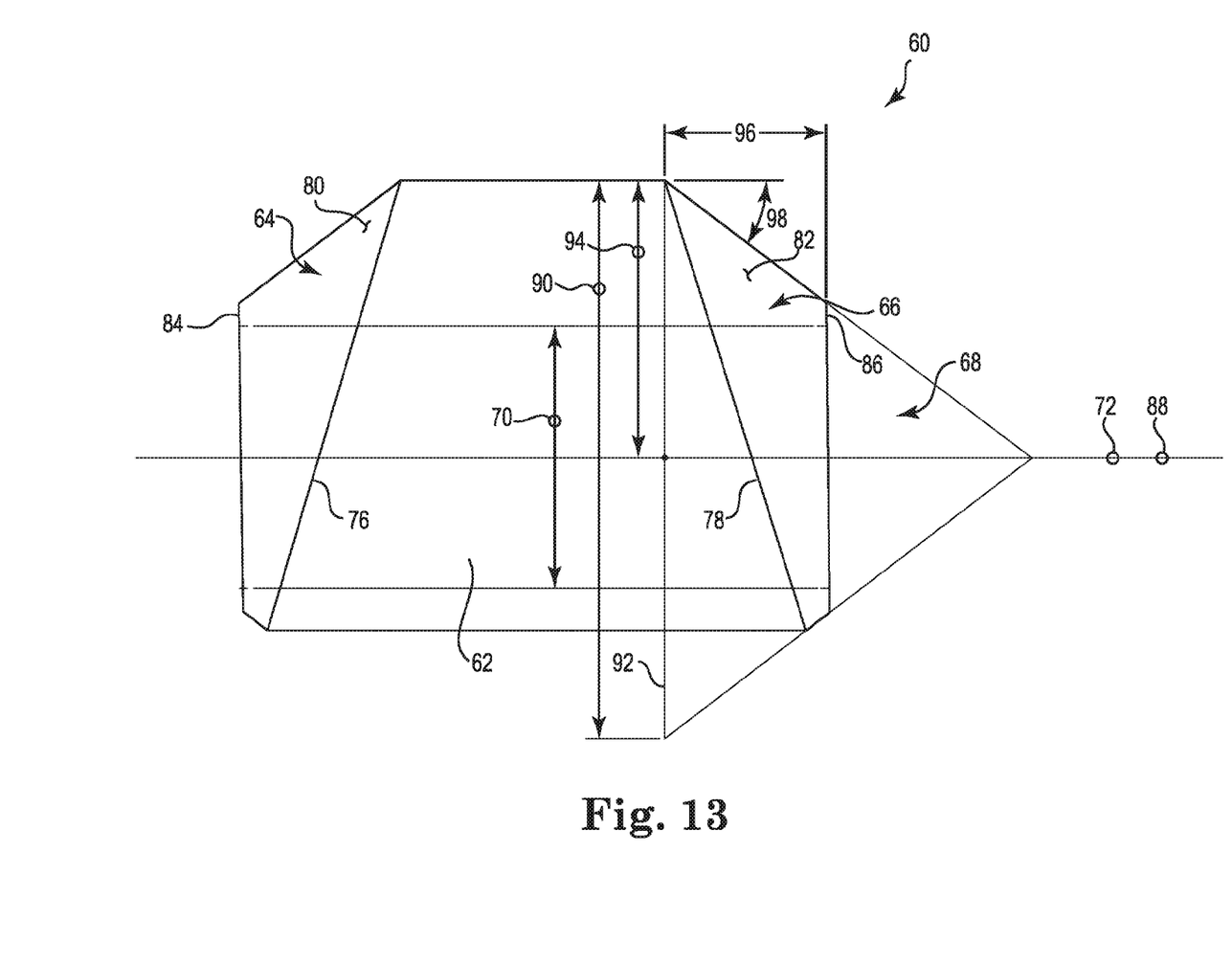
FIG. 13 is a side view thereof.

Each transition 76, 78 of the middle portion 62 to each end portion 64, 66 may be shaped, in part, based on the location of the bore 68. For example, when the bore 68 is centered in the middle portion 62 (i.e., longitudinal axes 72, 74 of the middle portion 62 and the bore 68 are aligned) each transition 76, 78 of the middle portion 62 to the end portions 64, 66 may be substantially perpendicular to the longitudinal axis 74 of the middle portion 62. That is, the transition 76, 78 from the substantially cylindrical middle portion 62 to the substantially conical end portion 64, 66 may be a circle that follows the outside surface of the cylindrical middle portion 62. However, where the bore 68 is offset from the center of the middle portion 62 as shown in FIGS. 12-14, each transition of the middle portion 62 may be substantially skewed to form a canted base of the conical end portion 64, 66 that is substantially elliptical as described in more detail below. As will be appreciated, the more offset the bore 68 is from the longitudinal axis 74 of the cylindrical middle portion 62, the more skewed the transition 76, 78 will be between the middle portion 62 and the end portions 64, 66.

The end portions 64, 66 may be arranged immediately adjacent to each end of the middle portion 62 and may be monolithic with the middle portion 62 or may be separate parts that are attached thereto via welding, soldering, brazing, adhering, or other securing methods or techniques. As shown in FIGS. 12-13, the end portions 64, 66 may include a portion of a frustrom of a cone with a canted base 76, 78, a conical outer surface 80, 82, and a truncated peak 84, 86.

As shown in FIGS. 12 and 13, the end portions 64, 66 may be a part of a cone frustrom that may be defined by a cone axis 88 that is located at and aligned with the longitudinal axis 72 of the bore 68. The diameter 90 of the theoretical base 92 of the cone frustrom may be approximately equal to two times the largest radial distance 94 from the outer cylindrical surface of the middle portion 62 to the longitudinal axis 72 of the bore 68 as shown in FIG. 14. The height 96 of the frustrom as measured parallel to the longitudinal axes 72, 74 of the middle portion 62 and the bore 68 may be selectable and may be similar in size to the diameter 70 of the bore 68, for example. Other heights 96 of the frustrom may also be provided. The cone frustrom may have a slope 98 relative to the surface of the middle portion 62 ranging from approximately 20 degrees to approximately 60 degrees, or from approximately 30 degrees to approximately 45 degrees, or from approximately 35 degrees to approximately 40 degrees, or a slope of approximately 38 degrees may be provided.

Having defined the cone frustroms of which the end portions 64, 66 are each a part, it will be appreciated that the truncated peaks 84, 86 may be substantially circular when viewed from the end and, as such, may be substantially perpendicular to the longitudinal axes 72, 74 of the middle portion 62 and the bore 68. The end surface of the head 60 may be substantially annularly shaped and bounded by the outer surface 80, 82 of the end portions 64, 66 on its outer rim and the diameter 70 of the bore 68 on its inner rim.

The canted base 76, 78 of the frustrom of the cone may extend across the head 60 (from the side directly opposite the side toward which the bore is shifted to the side toward which the bore is shifted) and may be canted so as to travel through substantially all of the height 96 (i.e., from the theoretical base to the truncated peak) of the frustrom of the cone as it extends from one side to the other. As such, the canted base 76, 78 may form a substantially elliptically shaped transition or boundary between the middle portion 62 and the frustrom-shaped end portions 64, 66.

The conical outer surface 80, 82 of the end portion 64, 66 may thus be formed by the portion of the cone frustrom that falls between the canted base 76, 78 and the truncated peak 84, 86. The conical outer surface 80, 82, like the cylindrical outer surface of the middle portion 62 may be substantially uninterrupted and continuous. In addition, the conical outer surface 80, 82 may be substantially smooth or an abrasive material may be provided thereon. In some embodiments, as shown, a portion of the middle portion 62 may be chamfered at an angle matching that of the conical outer surface 80, 82 of the end portion 64, 66 or the canted base 76, 78 may stop slightly short of the truncated peak 84, 86 such that a portion of the conical outer surface 80, 82 extends around the full circumference of the end portion 64, 66.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. An atherectomy device, comprising:
    an elongated, flexible drive shaft having an outer diameter sized for insertion into a vasculature of a patient and having a proximal end opposite a distal end, the proximal end remaining outside the vasculature of the patient, the drive shaft further comprising a tapered distal tip comprising a length and an outer diameter that is gradually decreasing from the drive shaft's outer diameter as the tapered distal tip extends distally to the distal end of the drive shaft;
    a handle coupled to the proximal end of the drive shaft for controlling the drive shaft; and
    a head arranged proximate the distal end of the drive shaft comprising a length that is slightly shorter than the length of the tapered distal tip, the head comprising:
        a middle portion having a substantially uninterrupted outer surface; and
        substantially conically-shaped first and second end portions, wherein the substantially conically-shaped end portions comprise a canted base, a truncated peak, and a conical outer surface and wherein the canted base of the first end portion extends from a side of the head opposite a longitudinal bore to a side of the head near the bore and travels through substantially the full height of the first end portion as it extends; and
        the bore having a diameter and extending through the middle portion and through the substantially conically-shaped end portions, wherein the bore is adapted to frictionally engage at least a portion of the drive shaft and the tapered distal tip of the drive shaft, and wherein a portion of the tapered distal tip extends outwardly distally from the head.

2. The device of claim 1, wherein the bore has a diameter slightly smaller than an outer diameter of the drive shaft.

3. The device of claim 1, wherein the substantially conically-shaped end portions comprise a portion of a frustrom of a cone.

4. The device of claim 1, wherein the conically-shaped end portions each have a height measured substantially along the longitudinal axes of the middle portion and the bore.

5. The device of claim 1, wherein the canted base of the second end portion extends from a side of the head opposite the bore to a side of the head near the bore and travels through substantially the full height of the second end portion as it extends.

6. The device of claim 5, wherein the head is symmetrical about a line extending transverse to the longitudinal axis of the bore.

7. The device of claim 1, wherein the canted base of each of the first and second end portions forms an elliptically-shaped transition between the middle portion and the respective end portion.

8. The device of claim 1, wherein the truncated peak comprises an annularly-shaped end bounded by the conical outer surface and the diameter of the bore.

\* \* \* \* \*